United States Patent [19]
Genard et al.

[11] Patent Number: 6,022,379
[45] Date of Patent: Feb. 8, 2000

[54] PYRROLE DERIVATIVES OF 1,4-NAPHTHOQUINONE AND OF 1,4-DIHYDROXYNAPHTHALENE FOR DYEING KERATIN FIBERS, COMPOSITIONS COMPRISING THE SAME, AND DYEING PROCESS

[75] Inventors: Sylvie Genard; Hervé Andrean; Michel Hocquaux, all of Paris, France

[73] Assignee: L'Oreal, Paris, France

[21] Appl. No.: 09/031,777

[22] Filed: Feb. 27, 1998

[30] Foreign Application Priority Data

Feb. 27, 1997 [FR] France .................................. 97 02370

[51] Int. Cl.⁷ ...................................... A61K 7/13
[52] U.S. Cl. ........................ 8/405; 8/574; 8/663; 8/673; 8/693; 548/418; 548/420; 548/427; 548/560; 548/561; 548/562; 548/563; 548/564

[58] Field of Search ................................ 8/405, 423, 574, 8/663, 673, 693; 548/541, 543, 551, 556, 562, 563, 564, 418, 420, 427, 560, 561

[56] References Cited

U.S. PATENT DOCUMENTS 4,684,599 8/1987 DoMinh et al. ..................... 430/270

*Primary Examiner*—Caroline D. Liott
*Attorney, Agent, or Firm*—Finnegan, Henderson, Farabow, Garrett & Dunner

[57] ABSTRACT

Pyrrole derivatives of 1,4-naphthoquinone and of 1,4-dihydroxynaphthalene, dye compositions containing them and the corresponding dyeing process.

26 Claims, No Drawings

PYRROLE DERIVATIVES OF 1,4-NAPHTHOQUINONE AND OF 1,4-DIHYDROXYNAPHTHALENE FOR DYEING KERATIN FIBERS, COMPOSITIONS COMPRISING THE SAME, AND DYEING PROCESS

The invention relates to the use of pyrrole derivatives of 1,4-naphthoquinone and of 1,4-dihydroxynaphthalene, as direct dyes in a dye composition intended for dyeing keratin substances, in particular in a cosmetic composition intended for dyeing human keratin substances, and in particular human keratin fibers such as the hair; the invention also relates to some of these pyrrole derivatives of 1,4-naphthoquinone and of 1,4-dihydroxynaphthalene as novel compounds.

In the journal, *Chemistry Express* 1990, Vol. 5, No. 10, pages 749–752, K. Yoshida et al. studied the reaction of 1,4-naphthoquinone with N-methylpyrrole. They obtained two colored products by selective synthesis: 2-(1-methyl-2-pyrrolyl)-1,4-naphthoquinone and 2,5-bis(1,4-naphthoquinon-2-yl)pyrrole, which can be used as dyestuffs.

However, the chemistry of pyrrolo-1,4-naphthoquinones has received very little coverage in the literature.

Thus, certain pyrrole derivatives of 1,4-naphthoquinone are known per se; such compounds, such as those corresponding to the formulae (a), (b), (c), (d) and (e) below were described as early as 1936 by P. Pratesi in the publication *Gazz. Chim. Ital.*, Vol. 66, pages 215–221 and in Beilstein Reg. Nos. 260480-246571-219671-21973-253008:

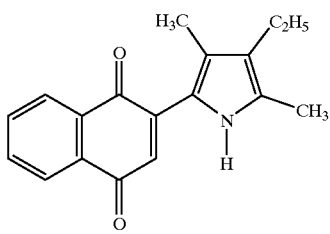
(a)

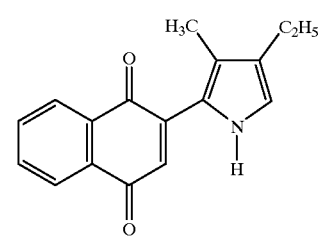
(b)

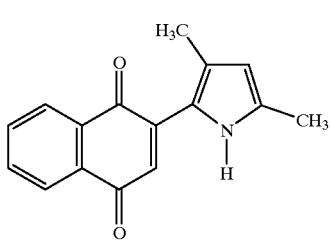
(c)

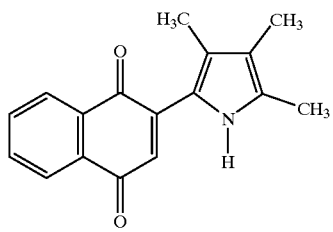
(d)

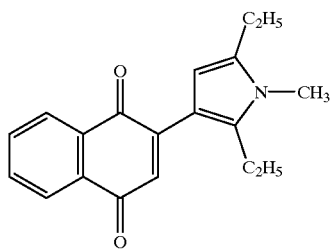
(e)

Others, synthesized photochemically, and corresponding to the formulae (f) and (g) below, were described by K. Maruyama et al. in the journal *Bull. Chem. Soc. Jpn.*, 1985, Vol. 58, pages 3049–3050:

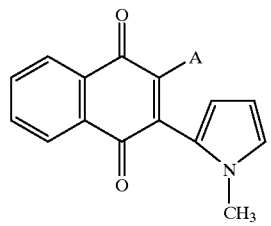
(f)

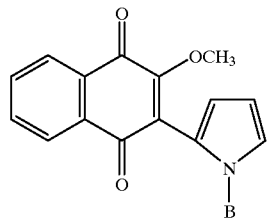
(g)

in which formulae (f) and (g):

A denotes H, $CH_3$, $OCH_3$, or Br, and

B denotes H, $CH_3$, $C_2H_5$, or $CH_2$—$C_6H_5$.

Since then, other pyrrole derivatives of 1,4-naphthoquinone, known per se, have been synthesized.

Thus, in the journal *J. Org. Chem.* 1985, Vol. 50, pages 5546–5550, T. Itahara et al. have described the reaction of 1,4-naphthoquinone with 1-(benzenesulphonyl)pyrrole in refluxing acetic acid, in the presence of palladium acetate, to form the compound of formula (h) below:

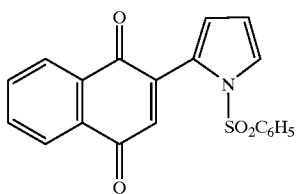

In the journal *Dyes and Pigments* 1991, Vol. 16, pages 309–315, M. Matsuoka has described and prepared the compound of formula (i) below:

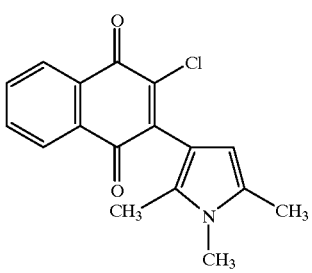

by reaction of 2,3-dichloro-1,4-naphthoquinone with 1,2,5-trimethyl-3-pyrrole in the presence of acidic alumina.

In the journal *Chemistry Letters* 1996, Vol. 2, pages 139–140, S. Yoshida et al., have described and prepared the compound of formula (k) below:

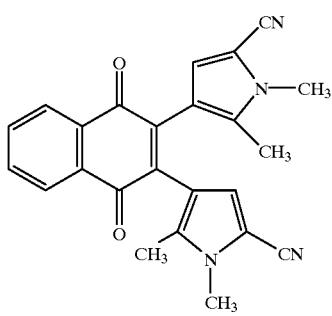

by reaction of 2,3-dibromo-1,4-naphthoquinone with 2-cyano-1,5-dimethyl-4-tributylstannylpyrrole in the presence of a palladium catalyst.

Among the pyrrolo-1,4-dihydroxynaphthalenes, only 2-(1-methyl-2-pyrrolyl)-1,4-dihydroxynaphthalene is known, which was disclosed as a chemical intermediate in the preparation of 2-(1-methyl-2-pyrrolyl)-1,4-naphthoquinone in the review *Chemistry Express* 1990—Vol. 5, No. 10, pages 750–751, already mentioned above.

In the field of hair dyeing, direct dyes are sought, i.e., dyes which, without supplying an oxidizing agent other than ambient air, are capable by themselves of temporarily modifying the natural shade of the hair. In this application, the dyes must satisfy a certain number of criteria and in particular must generate reproducible colorations in rich and varied shades, allowing a wide range of colors to be obtained which is capable of satisfying the formulator.

Among the direct dyes used conventionally to dye the hair, naphthoquinone dyes such as 2-hydroxynaphthoquinone (commonly known as lawsone), 5-hydroxynaphthoquinone (commonly known as juglone), 2-hydroxynaphthoquinones and 5-hydroxynaphthoquinones substituted with other hydroxyl radicals, chlorine atoms and alkoxy or alkyl radicals, as described in French patents FR-2,517,199 and FR-2,537,433, are already known.

However, the dyes do not yet make it possible to obtain a range which is sufficiently rich in varied shades.

After considerable research conducted in this matter, the inventors have now discovered a novel class of naphthoquinone dyes, pyrrole derivatives of 1,4-naphthoquinone and of 1,4-dihydroxynaphthalene, some of which are novel, which make it possible to dye keratin substances, especially human keratin substances and in particular human keratin fibers such as the hair, without an oxidizing agent. In addition, the hair colorings obtained using these dyes are in reproducible, intense and varied shades.

This discovery forms the basis of the present invention.

A subject of the present invention is thus the use, as direct dyes, in a composition intended for dyeing keratin substances, in particular a composition intended for dyeing human keratin substances, and in particular human keratin fibers such as the hair, of pyrrole derivatives of 1,4-naphthoquinone and of 1,4-dihydroxynaphthalene, characterized in that they correspond to one of the formulae (I) or (II) below:

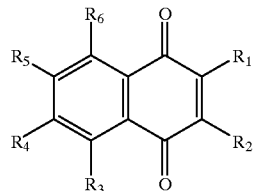

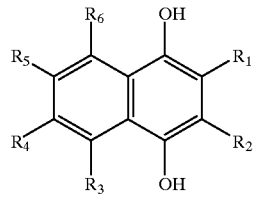

in which formulae (I) or (II):

$R_1$ and $R_2$ independently are selected from a hydrogen atom, a halogen atom, an OH radical, a $C_1$–$C_4$ alkyl radical, a $C_1$–$C_4$ alkoxy radical and a radical Z of formula (III) defined below, $R_3$ to $R_6$ independently are selected from a hydrogen atom, a halogen atom, an OH radical, a $C_1$–$C_4$ alkyl radical and a $C_1$–$C_4$ alkoxy radical, radical Z of formula (III) is defined as follows:

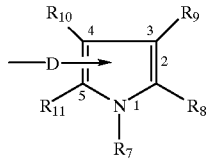

in which:

D is a covalent bond between the pyrrole ring (III) and the rings of structure (I) or (II), $R_7$ to $R_{11}$ independently denote hydrogen or an optionally substituted $C_1$–$C_{18}$ alkyl radical, a $CH_2$—$C_6H_5$ a $SO_2$—$C_6H_5$ radical, a radical $CO(C_1$–$C_4)$alkyl, or COOH and its salts, or $COO(C_1$–$C_4)$alkyl, or CONR'R" with R' and R" independently denoting H or $C_1$–$C_4$ alkyl, a $C_6H_5$ radical which may be substituted with one or more halogen atoms or one or more hydroxyl, $C_1$–$C_4$ alkyl or $C_1$–$C_4$ alkoxy radicals, and $R_8$ to $R_{11}$ also denote at least one bond D, it being understood (i) that at least one of the radicals $R_1$ or $R_2$ denotes a radical Z, (ii) that the attachment of Z to the rings of formulae (I) or (II) is carried out on any of the positions 2 to 5 of the pyrrole ring, (iii) and that the radicals $R_8$ and $R_{10}$ or the radicals $R_9$ and $R_{11}$ do not simultaneously denote a compound of formula (I).

The $C_1$–$C_4$ alkyl radicals or the $C_1$–$C_4$ alkyl radicals of the alkoxy radicals or of the acyl radicals can be linear or branched, saturated or unsaturated and can be selected in particular from the methyl, ethyl, n-propyl, isopropyl, n-butyl, isobutyl and tert-butyl radicals, and more particularly methyl.

The $C_1$–$C_{18}$ alkyl radicals can be linear or branched, saturated or unsaturated; they can be substituted with one or more halogen atoms, one or more hydroxyl radicals, free or protected by an ether function selected from aliphatic ethers such as methoxymethyl ether, methyl ether or ethyl ether, aromatic ethers such as benzyl ether, alkylsilyl ethers such as trimethylsilyl ether or tert-butyldimethylsilyl ether, alkylarylsilyl ethers such as tert-butyldiphenylsilyl ether or alternatively from aliphatic esters such as acetates and aromatic esters such as benzoates.

These $C_1$–$C_{18}$ alkyl radicals can also be substituted with one or more radicals CN, COOR, NR'R" and the addition salts thereof with an acid, N(R')COR" and CONR'R", in which R, R' and R" denote H or $C_1$–$C_4$ alkyl defined above.

The $C_1$–$C_{18}$ alkyl radicals are selected in particular, for example, from the methyl, ethyl, n-propyl, isopropyl, n-butyl, isobutyl, tert-butyl, n-pentyl, isopentenyl, n-octyl and n-hexadecyl radicals, and more particularly methyl, tert-butyl, n-pentyl, isopentenyl, n-octyl and n-hexadecyl.

The substitution radicals for the $C_1$–$C_{18}$ alkyl radicals which denote COOH, as well as the COOH radicals of $R_7$ to $R_{11}$ can also be salified by non-toxic cations selected from alkali-metal, alkaline-earth metal and ammonium cations.

The halogen atoms are selected in particular from chlorine and bromine.

Among the pyrrole derivatives of formulae (I) and (II) defined above, mention may be made in particular of the following compounds:

2,3-bis(1,5-dimethyl-2-cyano-1H-pyrrol-4-yl)-[1,4]-naphthoquinone,
2-(1,2,5-trimethyl-1H-pyrrol-4-yl)-3-chloro-[1,4]-naphthoquinone,
2-(1,2,5-trimethyl-1H-pyrrol-4-yl)-[1,4]-naphthoquinone,
2-(4-ethyl-3,5-dimethyl-1H-pyrrol-2-yl)-[1,4]-naphthoquinone,
2-(1-benzyl-1H-pyrrol-2-yl)-3-methoxy-[1,4]-naphthoquinone,
2-(1-methyl-1H-pyrrol-2-yl)-3-methoxy-[1,4]-naphthoquinone,
2-(1-ethyl-1H-pyrrol-2-yl)-3-methoxy-[1,4]-naphthoquinone,
2-(1H-pyrrol-2-yl)-3-methoxy-[1,4]-naphthoquinone,
2-(1-methyl-1H-pyrrol-2-yl)-3-bromo-[1,4]-naphthoquinone,
2-(1-methyl-1H-pyrrol-2-yl)-3-methyl-[1,4]-naphthoquinone,
2-(1-benzenesulphonyl-1H-pyrrol-2-yl)-[1,4]-naphthoquinone,
2-(2,5-dimethyl-1H-pyrrol-3-yl)-[1,4]-naphthoquinone,
2-(1-pentyl-1H-pyrrol-2-yl)-[1,4]-naphthoquinone,
2-(1-octyl-1H-pyrrol-2-yl)-[1,4]-naphthoquinone,
2-(1-hexadecyl-1H-pyrrol-2-yl)-[1,4]-naphthoquinone,
2-(1-benzyl-1H-pyrrol-2-yl)-[1,4]-naphthoquinone,
3-[2-(1,4-dioxo-1,4-dihydronaphthalen-2-yl)-pyrrol-1-yl] propionitrile,
methyl [5-(1,4-dioxo-1,4-dihydronaphthalen-2-yl)-1-methyl-1H-pyrrol-2-yl]acetate,
methyl 4-(1,4-dioxo-1,4-dihydronaphthalen-2-yl)-2,5-dimethyl-1H-pyrrole-3-carboxylate,
methyl 4-(1,4-dioxo-1,4-dihydronaphthalen-2-yl)-1,2,5-trimethyl-1H-pyrrole-3-carboxylate,
2-(2,5-dimethyl-1H-pyrrol-3-yl)-8-hydroxy-[1,4]-naphthoquinone,
methyl 4-(8-hydroxy-1,4-dioxo-1,4-dihydronaphthalen-2-yl)-1,2,5-trimethyl-1H-pyrrole-3-carboxylate,
methyl 4-(8-hydroxy-1,4-dioxo-1,4-dihydronaphthalen-2-yl)-2,5-dimethyl-1H-pyrrole-3-carboxylate,
2-(1H-pyrrol-2-yl)-[1,4]-naphthoquinone,
2-(1-methyl-1H-pyrrol-2-yl)-[1,4]-naphthoquinone,
N-{2-[2-(1,4-dioxo-1,4-dihydronaphthalen-2-yl)pyrrol-1-yl]ethyl}acetamide,
2-{N-[(2-hydroxy-1-hydroxymethyl-1-methyl)ethyl]-1H-pyrrol-2-yl}-[1,4]-naphthoquinone,
2-[N-(β-hydroxyethyl)-1H-pyrrol-2-yl]-[1,4]-naphthoquinone,
2-carboxymethyl-5-(1,4-dioxo-1,4-dihydronaphthalen-2-yl)-1,4-dimethyl-1H-pyrrole-3-carboxylic acid,
4-(1,4-dioxo-1,4-dihydronaphthalen-2-yl)-2,5-dimethyl-1H-pyrrole-3-carboxylic acid,
ethyl 4-(1,4-dioxo-1,4-dihydronaphthalen-2-yl)-3,5-dimethyl-1H-pyrrole-2-carboxylate,
2-(4-acetyl-3,5-dimethyl-1H-pyrrol-2-yl)-[1,4]-naphthoquinone,
2-(1-methyl-1H-pyrrol-2-yl)-[1,4]-dihydroxynaphthalene,
methyl [5-(1,4-dihydroxynaphthalen-2-yl)-1-methyl-1H-pyrrol-2-yl]acetate.

Among the pyrrole derivatives of 1,4-naphthoquinone which can be used according to the present invention, the ones more particularly preferred are the derivatives of formula (I) for which:

$R_1$ is a radical Z of formula (III) for which $R_7$ is hydrogen, methyl, n-pentyl, isopentenyl, n-octyl, n-hexadecyl, $CH_2$—$C_6H_5$, $(CH_2)_2$—CN, $(CH_2)_2$—OH, $(CH_2)_2$—NH—$COCH_3$, or $C(CH_3)(CH_2OH)_2$, $R_8$ is hydrogen, $CH_3$, $COOC_2H_5$, $CH_2$—COOH, $CH_2$—$COOCH_3$, 2-(1,4-naphthoquinonyl), or 2-(8-hydroxy-1,4-naphthoquinonyl), $R_9$ is hydrogen, $CH_3$, $C_2H_5$, $COCH_3$, COOH or $COOCH_3$, $R_{10}$ is hydrogen, $CH_3$, 2-(1,4-naphthoquinonyl) or 2-(8-hydroxy-1,4-naphthoquinonyl), $R_{11}$ is $CH_3$, 2-(1,4-naphthoquinonyl) or 2-(8-hydroxy-1,4-naphthoquinonyl), $R_2$ is hydrogen, $R_3$ to $R_5$ are hydrogen, $R_6$ is hydrogen or an OH radical and even more particularly the following compounds:

2-(1H-pyrrol-2-yl)-[1,4]-naphthoquinone,
2-(1-methyl-1H-pyrrol-2-yl)-[1,4]-naphthoquinone,
2-(1-pentyl-1H-pyrrol-2-yl)-[1,4]-naphthoquinone,
2-(1-octyl-1H-pyrrol-2-yl)-[1,4]-naphthoquinone,
2-(1-hexadecyl-1H-pyrrol-2-yl)-[1,4]-naphthoquinone, 2-(1-benzyl-1H-pyrrol-2-yl)-[1,4]-naphthoquinone,
2-(4-ethyl-3,5-dimethyl-1H-pyrrol-2-yl)-[1,4]-naphthoquinone,
3-[2-(1,4-dioxo-1,4-dihydronaphthalen-2-yl)pyrrol-1-yl]propionitrile,
1-methyl-2,5-bis(1,4-naphthoquinon-2-yl)pyrrole,
1-pentyl-2,5-bis(1,4-naphthoquinon-2-yl)pyrrole,
1-octyl-2,5-bis(1,4-naphthoquinon-2-yl)pyrrole,
1-hexadecyl-2,5-bis(1,4-naphthoquinon-2-yl)pyrrole,
1-benzyl-2,5-bis(1,4-naphthoquinon-2-yl)pyrrole,
methyl [5-(1,4-dioxo-1,4-dihydronaphthalen-2-yl)-1-methyl-1H-pyrrol-2-yl]acetate,
methyl 4-(1,4-dioxo-1,4-dihydronaphthalen-2-yl)-2,5-dimethyl-1H-pyrrole-3-carboxylate,
methyl 4-(1,4-dioxo-1,4-dihydronaphthalen-2-yl)-1,2,5-trimethyl-1H-pyrrole-3-carboxylate,
2-(2,5-dimethyl-1H-pyrrol-3-yl)-8-hydroxy-[1,4]-naphthoquinone,
methyl 4-(8-hydroxy-1,4-dioxo-1,4-dihydronaphthalen-2-yl)-1,2,5-trimethyl-1H-pyrrole-3-carboxylate,
methyl 4-(8-hydroxy-1,4-dioxo-1,4-dihydronaphthalen-2-yl)-2,5-dimethyl-1H-pyrrole-3-carboxylate,
N-{2-[2-(1,4-dioxo-1,4-dihydronaphthalen-2-yl)pyrrol-1-yl]ethyl}acetamide,
2-{N-[(2-hydroxy-1-hydroxymethyl-1-methyl)ethyl]-1H-pyrrol-2-yl}-[1,4]-naphthoquinone,
2-[N-(β-hydroxyethyl)-1H-pyrrol-2-yl]-[1,4]-naphthoquinone,
2-carboxymethyl-5-(1,4-dioxo-1,4-dihydronaphthalen-2-yl)-1,4-dimethyl-1H-pyrrole-3-carboxylic acid,
4-(1,4-dioxo-1,4-dihydronaphthalen-2-yl)-2,5-dimethyl-1H-pyrrole-3-carboxylic acid,
ethyl 4-(1,4-dioxo-1,4-dihydronaphthalen-2-yl)-3,5-dimethyl-1H-pyrrole-2-carboxylate, and
2-(4-acetyl-3,5-dimethyl-1H-pyrrol-2-yl)-[1,4]-naphthoquinone.

Among the pyrrole derivatives of 1,4-dihydroxynaphthalene which can be used according to the present invention, 2-(1-methyl-1H-pyrrol-2-yl)-[1,4]-dihydroxynaphthalene and methyl [5-(1,4-dihydroxynaphthalen-2-yl)-1-methyl-1H-pyrrol-2-yl]acetate are more particularly preferred.

In order to prepare the dyes of formulae (I) and (II), the process may be performed conventionally, according to the scheme described by K. Yoshida et al. in the article *Chemistry Express*, 1990, Vol. 5, No. 10, pages 749–752, the disclosure of which is specifically incorporated by reference herein, by reaction of 1,4-naphthoquinone with pyrrole derivatives (corresponding to the desired dye of formula (I) or (II)), and by selecting a suitable molar ratio between the two reactants, in a solvent medium and in the presence or absence of a catalyst; however, in order to prepare the dyes of formula (II), the process is always performed in the absence of an oxidation catalyst.

The compounds of formula (I) can also be prepared by carrying out a standard oxidation reaction on the compounds of formula (II). Similarly, the compounds of formula (II) can be prepared by a standard reduction reaction on the compounds of formula (I).

Among the compounds of formulae (I) and (II) of the invention, some are known per se, in particular those described in the articles mentioned above. Others are novel and constitute another subject of the present invention.

The subject of the present invention is thus novel compounds of formula (I) defined above, comprising all the compounds of formula (I) except the following:
2-(1-benzenesulphonyl-1H-pyrrol-2-yl)-[1,4]-naphthoquinone,
2-(1-benzyl-1H-pyrrol-2-yl)-3-methoxy-[1,4]-naphthoquinone,
2-(1-ethyl-1H-pyrrol-2-yl)-3-methoxy-[1,4]-naphthoquinone,
2-(1H-pyrrol-2-yl)-3-methoxy-[1,4]-naphthoquinone,
2-(1-methyl-1H-pyrrol-2-yl)-3-bromo-[1,4]-naphthoquinone,
2-(1-methyl-1H-pyrrol-2-yl)-3-methyl-[1,4]-naphthoquinone,
2-(1-methyl-1H-pyrrol-2-yl)-3-methoxy-[1,4]-naphthoquinone,
2-(1,2,5-trimethyl-1H-pyrrol-4-yl)-3-chloro-[1,4]-naphthoquinone,
as well as compounds of formula (IV) below:

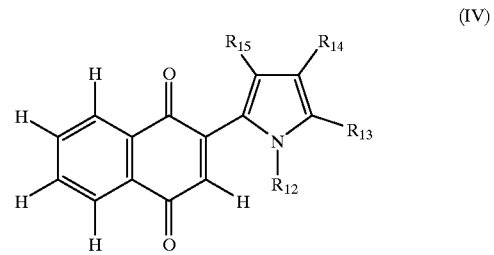

in which:
$R_{12}$ denotes H, alkyl, aryl or aralkyl and
$R_{13}$, $R_{14}$ and $R_{15}$ independently are H, alkyl, aryl, sulphonyl substituted with an alkyl or an aryl.

These novel compounds of formula (I) are selected more particularly from the following: 2-(1,2,5-trimethyl-1H-pyrrol-4-yl)-[1,4]-naphthoquinone,
3-[2-(1,4-dioxo-1,4-dihydronaphthalen-2-yl)pyrrol-1-yl]propionitrile,
methyl [5-(1,4-dioxo-1,4-dihydronaphthalen-2-yl)-1-methyl-1H-pyrrol-2-yl]acetate,
methyl 4-(1,4-dioxo-1,4-dihydronaphthalen-2-yl)-2,5-dimethyl-1H-pyrrole-3-carboxylate,
methyl 4-(1,4-dioxo-1,4-dihydronaphthalen-2-yl)-1,2,5-trimethyl-1H-pyrrole-3-carboxylate,
2-(2,5-dimethyl-1H-pyrrol-3-yl)-8-hydroxy-[1,4]-naphthoquinone,
methyl 4-(8-hydroxy-1,4-dioxo-1,4-dihydronaphthalen-2-yl)-1,2,5-trimethyl-1H-pyrrole-3-carboxylate,
methyl 4-(8-hydroxy-1,4-dioxo-1,4-dihydronaphthalen-2-yl)-2,5-dimethyl-1H-pyrrole-3-carboxylate,
2-(2,5-dimethyl-1H-pyrrol-3-yl)-[1,4]-naphthoquinone,
2-[1-(β-hydroxyethyl)-1H-pyrrol-2-yl]-[1,4]-naphthoquinone,
2-{N-[(2-hydroxy-1-hydroxymethyl-1-methyl)ethyl]-1H-pyrrol-2-yl}-[1,4]-naphthoquinone,
N-{2-[2-(1,4-dioxo-1,4-dihydronaphthalen-2-yl)pyrrol-1-yl]ethyl}acetamide,
2-carboxymethyl-5-(1,4-dioxo-1,4-dihydronaphthalen-2-yl)-1,4-dimethyl-1H-pyrrole-3-carboxylic acid,
4-(1,4-dioxo-1,4-dihydronaphthalen-2-yl)-2,5-dimethyl-1H-pyrrole-3-carboxylic acid,
ethyl 4-(1,4-dioxo-1,4-dihydronaphthalen-2-yl)-3,5-dimethyl-1H-pyrrole-2-carboxylate, and
2-(4-acetyl-3,5-dimethyl-1H-pyrrol-2-yl)-[1,4]-naphthoquinone.

A subject of the present invention is also compounds that are selected from the following:
2-(1H-pyrrol-2-yl)-[1,4]-naphthoquinone,
2-(1-pentyl-1H-pyrrol-2-yl)-[1,4]-naphthoquinone,
2-(1-octyl-1H-pyrrol-2-yl)-[1,4]-naphthoquinone, 2-(1-hexadecyl-1H-pyrrol-2-yl)-[1,4]-naphthoquinone,
2-(1-benzyl-1H-pyrrol-2-yl)-[1,4]-naphthoquinone,
1-pentyl-2,5-bis(1,4-naphthoquinon-2-yl)pyrrole,
1-octyl-2,5-bis(1,4-naphthoquinon-2-yl)pyrrole,
1-hexadecyl-2,5-bis(1,4-naphthoquinon-2-yl)pyrrole, or
1-benzyl-2,5-bis(1,4-naphthoquinon-2-yl)pyrrole.

A subject of the present invention is also novel compounds of formula (II) defined above, comprising all of the compounds of formula (II) except for the following compound:
2-(1-methyl-1H-pyrrol-2-yl)-[1,4]-dihydroxynaphthalene.

A novel compound of formula (II) which is more particularly preferred is methyl [5-(1,4-dihydroxynaphthalen-2-yl)-1-methyl-1H-pyrrol-2-yl]acetate.

A subject of the invention is also a dye composition for keratin substances which comprises, in a medium which is suitable for dyeing, an effective amount of at least one compound of formula (I) or (II) defined above.

A subject of the invention is also a cosmetic composition intended for dyeing human keratin substances, and even more particularly for dyeing human keratin fibers such as the hair, comprising, in a cosmetically acceptable medium, an effective amount of at least one compound of formula (I) or (II) defined above.

A subject of the invention is also the dyeing processes using these compositions.

However, other characteristics, aspects and advantages of the invention will become even more apparent on reading the description which follows, as well as the various concrete, but in no way limiting, examples intended to illustrate it.

For the purposes of the invention, the term keratin substances is understood mainly to refer to natural textile fibers such as wool and animal fur, the term human keratin substances is understood to refer to the skin and the nails, and the term human keratin fibers is understood to refer to head hair, other hairs, the eyelashes and the eyebrows. The invention relates more particularly to human keratin substances, and even more particularly to the hair.

The compounds of formula (I) or (II) are generally present in proportions ranging from approximately 0.01 to approximately 10% by weight, more preferably from approximately 0.05 to approximately 5% by weight, relative to the total weight of the dye composition.

The compounds of formula (I) or (II) can also be incorporated into dye compositions for oxidation dyeing which contain oxidation bases and optionally couplers, in order to enrich with glints the shades obtained with the oxidation dyes.

The cosmetically acceptable medium is preferably a medium comprising water and/or cosmetically acceptable organic solvents if the composition is cosmetic, and more particularly alcohols (ethyl alcohol, isopropyl alcohol, benzyl alcohol and phenylethyl alcohol), glycols or glycol ethers (propylene glycol or its ethers such as, for example, propylene glycol monomethyl ether, butylene glycol, dipropylene glycol and diethylene glycol alkyl ethers such as, for example, diethylene glycol monoethyl ether or monobutyl ether, ethylene glycol monomethyl, monoethyl and monobutyl ethers), in concentrations preferably ranging from approximately 0.5 to approximately 25% by weight, and more preferably from 2 to 15% by weight, relative to the total weight of the composition.

The medium can also contain fatty substances such as oils and waxes.

Fatty amides such as mono- and diethanolamides of coconut-derived acids, of lauric acid or of oleic acid can also be added to the composition according to the invention in concentrations preferably of approximately 0.05 to approximately 10% by weight.

Besides the dyes of formula (I) or (II), the dye composition according to the invention can also contain, in order to obtain varied shades, other direct dye(s) used conventionally, and in particular nitrobenzene dyes, such as nitrophenylenediamines, nitrodiphenylamines, nitroanilines, nitrophenol ethers or nitrophenols, nitropyridines, anthraquinone dyes, mono- or diazo dyes, triarylmethane dyes, azine dyes, acridine dyes and xanthene dyes, or alternatively metalliferous dyes.

The proportion of all of these other additional direct dyes can preferably range from approximately 0.05 to approximately 10% by weight relative to the total weight of the dye composition.

The dye composition can also contain any other adjuvant usually used for dyeing keratin substances, and, for example, surfactants that are well known in the state of the art and of anionic, cationic, nonionic, amphoteric or zwitterionic type or mixtures thereof, thickeners, antioxidants, fragrances, sequestering agents, dispersing agents, conditioners, preserving agents, opacifiers, etc.

Needless to say, a person skilled in the art will take care to select the optional complementary compound(s) mentioned above such that the advantageous properties intrinsically associated with the dye composition according to the invention are not, or are not substantially, adversely affected by the addition(s) envisaged.

The dye composition according to the invention can be formulated at acidic, neutral or alkaline pH, it being possible for the pH to range, for example, preferably from 2 to 11 and more preferably from 2.5 to 10, and for it to be adjusted using basifying agents or acidifying agents that are previously well known.

Among the basifying agents, mention may be made, for example, of aqueous ammonia, alkaline carbonates, alkanolamines such as mono-, di- and triethanolamines and derivatives thereof, sodium hydroxide, potassium hydroxide and compounds of the following formula:

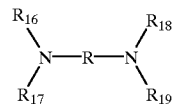

in which:

R is a propylene residue optionally substituted with a hydroxyl group or a $C_1$–$C_4$ alkyl radical; $R_{16}$, $R_{17}$, $R_{18}$ and $R_{19}$ independently represent a hydrogen atom or a $C_1$–$C_4$ alkyl or $C_1$–$C_4$ hydroxyalkyl radical.

The acidifying agents are, conventionally, by way of example, inorganic or organic acids such as hydrochloric acid, orthophosphoric acid, carboxylic acids such as tartaric acid, citric acid or lactic acid, or sulphonic acids.

When the composition is intended to be applied to human keratin fibers, it can be in various forms, such as in the form of a liquid, a cream, a gel or any other form which is suitable for dyeing keratin fibers. In particular, it can be packaged under pressure in an aerosol can in the presence of a propellant and can form a mousse.

The compositions for the nails and the skin are, in particular, nail varnishes, make-up products for the lips or the face such as lipsticks, eyeshadows, blushers, foundations, eyeliners or mascaras.

Another subject of the invention relates to a process for dyeing human keratin fibers, and more particularly the hair, by direct dyeing, this process consisting in leaving a dye composition containing at least one compound of formula (I) or (II) to act on wet or dry keratin fibers. The composition according to the invention can be used as a leave-in composition, i.e. after the composition has been applied to the fibers, they are dried without intermediate rinsing. In the other modes of application, the composition is left to act on the fibers for an exposure time ranging from approximately 3 to approximately 60 minutes, more preferably from approximately 5 to approximately 45 minutes, the fibers are rinsed, optionally washed, rinsed again and then dried.

Several examples of the preparation of compounds of formula (I) and (II) according to the invention, and concrete examples of dyeing based on such compounds, will now be given by way of illustration and with no limiting nature.

PREPARATION EXAMPLES

Example 1: Preparation of 2-(1-Methyl-1H-pyrrol-2-yl)-[1,4]-naphthoquinone

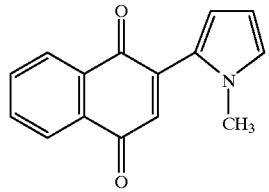

According to the procedure described in the article *Chemistry Express* 1990, Vol. 5, No. 10, pages 749–752, the disclosure of which is specifically incorporated by reference herein, 3.16 millimol of 1,4-naphthoquinone were stirred with 25 millimol of N-methylpyrrole and 3.16 millimol of copper acetate in 50 ml of acetic acid in a round-bottomed flask at room temperature for 1 hour. The reaction mixture was diluted with 300 ml of dichloromethane and the resulting mixture was then poured into a large volume of water (300 ml). The organic phase was then separated out and washed four times with 100 ml of water and finally with saturated aqueous NaCl solution. The resulting organic phase was dried over $Na_2SO_4$ and then concentrated under vacuum. The product 2-(1-methyl-1H-pyrrol-2-yl)-[1,4]-naphthoquinone was thus isolated in a yield of 79% after purification by chromatography on a column of silica.

$^1$H NMR 200 MHz (DMSO-$d_6$, δ ppm): 3.68 (s, 3H), 6.18 (d.d, 1H), 6.61 (d.d, 1H), 6.95 (s, 1H), 7.11 (m, 1H), 7.8 to 8.1 (m, 4H). Melting point: 95–96° C.

Example 2: Preparation of 2-(1-Pentyl-1H-pyrrol-2-yl)-[1,4]-naphthoquinone

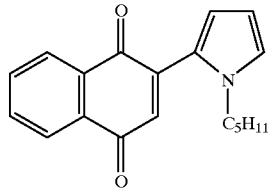

6.32 millimol of 1,4-naphthoquinone and 3.16 millimol of N-pentylpyrrole were stirred in 50 ml of chloroform in a round-bottomed flask for 5 hours at room temperature, the reaction being catalysed by addition of a few milligrams of para-toluenesulphonic acid. The reaction medium was diluted with 50 ml of chloroform and then washed four times with 50 ml of water and finally with saturated aqueous NaCl solution. The resulting organic phase was dried over $Na_2SO_4$ and then concentrated under vacuum. The product 2-(1-pentyl-1H-pyrrol-2-yl)-[1,4]-naphthoquinone was thus isolated, in the form of an oil, in a yield of 26% after purification by chromatography on a column of silica.

$^1$H NMR 200 MHz (CDCl$_3$, δ ppm): 0.85 (t, 3H), 1.16 to 1.34 (m, 4H), 1.65 to 1.80 (m, 2H), 3.95 (t, 2H), 6.28 (d.d, 1H), 6.60 (d.d, 1H), 6.88 (s, 1H), 6.97 (m, 1H), 7.72 to 7.81 (m, 2H), 8.09 to 8.19 (m, 2H).

Example 3: Preparation of 2-(1-Octyl-1H-pyrrol-2-yl)-[1,4]-naphthoquinone

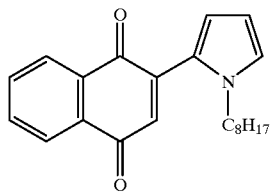

6.32 millimol of 1,4-naphthoquinone and 3.16 millimol of N-octylpyrrole were stirred in 50 ml of chloroform in a round-bottomed flask for 5 hours at room temperature, the reaction being catalysed by addition of a few milligrams of para-toluenesulphonic acid. The reaction medium was diluted with 50 ml of chloroform and then washed four times with 50 ml of water and finally with saturated aqueous NaCl solution. The resulting organic phase was dried over $Na_2SO_4$ and then concentrated under vacuum. The product 2-(1-octyl-1H-pyrrol-2-yl)-[1,4]-naphthoquinone was thus isolated, in the form of an oil, in a yield of 32% after purification by chromatography on a column of silica.

Example 4: Preparation of 2-(1-Hexadecyl-1H-pyrrol-2-yl)-[1,4]-naphthoquinone

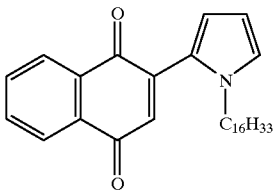

6.32 millimol of 1,4-naphthoquinone and 3.16 millimol of N-hexadecylpyrrole were stirred in 50 ml of chloroform in a round-bottomed flask for 5 hours at room temperature, the reaction being catalysed by addition of a few milligrams of para-toluenesulphonic acid. The reaction medium was diluted with 50 ml of chloroform and then washed four times with 50 ml of water and finally with saturated aqueous NaCl solution. The resulting organic phase was dried over $Na_2SO_4$ and then concentrated under vacuum. The product 2-(1-hexadecyl-1H-pyrrol-2-yl)-[1,4]-naphthoquinone was thus isolated in a yield of 41% after purification by chromatography on a column of silica.

$^1$H NMR 200 MHz (CDCl$_3$, δ ppm): 0.9 (t, 3H), 1.05 to 1.45 (m, 26H), 1.75 (m, 2H), 3.94 (t, 2H), 6.28 (d.d, 1H), 6.59 (d.d, 1H), 6.88 (s, 1H), 6.96 (m, 1H), 7.74 to 7.80 (m, 2H), 8.10 to 8.19 (m, 2H). Melting point: 56–57° C.

Example 5: Preparation of 2-(1-Benzyl-1H-pyrrol-2-yl)-[1,4]-naphthoquinone

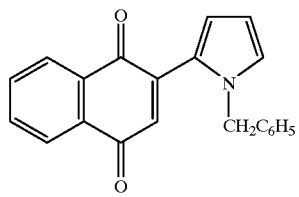

3.16 millimol of 1,4-naphthoquinone were stirred with 25 millimol of N-benzylpyrrole and 3.16 millimol of copper acetate in 50 ml of acetic acid in a round-bottomed flask at room temperature for 1 hour. The reaction mixture was diluted with 300 ml of dichloromethane and the resulting mixture was then poured into a large volume of water (300 ml). The organic phase was then separated out and washed four times with 100 ml of water and finally with saturated aqueous NaCl solution. The resulting organic phase was dried over $Na_2SO_4$ and then concentrated under vacuum. The product 2-(1-benzyl-1H-pyrrol-2-yl)-[1,4]-naphthoquinone was thus isolated in a yield of 18% after purification by chromatography on a column of silica.

Melting point: 99° C.

Example 6: Preparation of 3-[2-(1,4-Dioxo-1,4-dihydronaphthalen-2-yl)pyrrol-1-yl]propionitrile

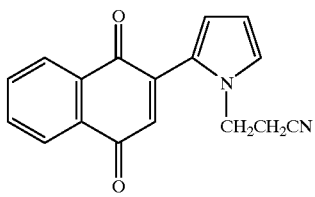

6.32 millimol of 1,4-naphthoquinone and 3.16 millimol of 3-(1-pyrrolyl) propionitrile were stirred in 50 ml of chloroform in a round-bottomed flask for 5 hours at room temperature, the reaction being catalysed by addition of a few milligrams of para-toluenesulphonic acid. The reaction medium was diluted with 50 ml of chloroform and then washed four times with 50 ml of water and finally with saturated aqueous NaCl solution. The resulting organic phase was dried over $Na_2SO_4$ and then concentrated under vacuum. The product 3-[2-(1,4-dioxo-1,4-dihydronaphthalen-2-yl)pyrrol-1-yl]propionitrile was thus isolated in a yield of 42% after purification by chromatography on a column of silica.

Melting point: 127–128° C.

Example 7: Preparation of 1-Methyl-2,5-bis(1,4-naphthoquinon-2-yl)pyrrole

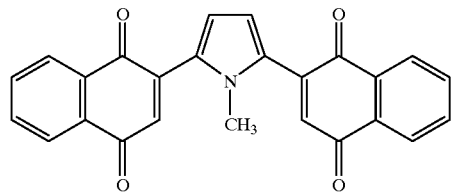

The procedure described in the article *Chemistry Express* 1990, Vol. 5, No. 10, pages 749–752, the disclosure of which is specifically incorporated by reference herein, was followed, by stirring 10 millimol of 1,4-naphthoquinone with 2.5 millimol of N-methylpyrrole in 40 ml of acetic acid at 50° C. for 5 hours. The reaction mixture was diluted with 300 ml of dichloromethane and the resulting mixture was then poured into a large volume of water (300 ml). The organic phase was then separated out and washed four times with 100 ml of water and finally with saturated aqueous NaCl solution. The resulting organic phase was dried over $Na_2SO_4$ and then concentrated under vacuum. The 1-methyl-2,5-bis(1,4-naphthoquinon-2-yl)pyrrole was thus obtained in a yield of 90%.

Melting point: 320–321° C.

Example 8: Preparation of 1-Pentyl-2,5-bis(1,4-naphthoquinon-2-yl)pyrrole

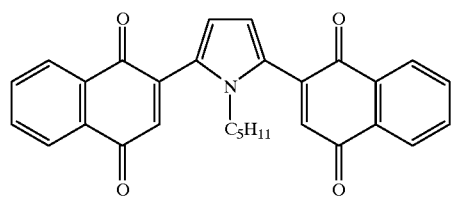

The same procedure as in Example 7 was followed by stirring 10 millimol of 1,4-naphthoquinone with 2.5 millimol of N-pentylpyrrole in 40 ml of acetic acid at 50° C. for 5 hours. The 1-pentyl-2,5-bis(1,4-naphthoquinon-2-yl)pyrrole was thus obtained in a yield of 87% after chromatography on a column of silica.

$^1$H NMR 200 MHz (CDCl$_3$, δ ppm): 0.62 (t, 3H), 0.8 to 1.4 (m, 6H), 4.0 (t, 2H), 6.63 (s, 2H), 7.06 (s, 2H), 7.75 to 7.85 (m, 4H), 8.06 to 8.23 (m, 4H). Melting point: 128° C.

Example 9: Preparation of 1-Octyl-2,5-bis(1,4-naphthoquinon-2-yl)pyrrole

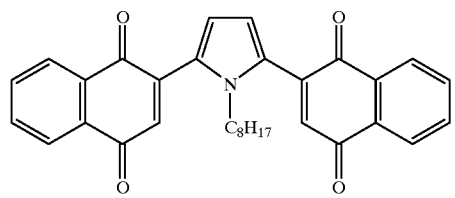

The same procedure as in Example 7 was followed by stirring 10 millimol of 1,4-naphthoquinone with 2.5 millimol of N-octylpyrrole in 40 ml of acetic acid at 50° C. for 5 hours. The 1-octyl-2,5-bis(1,4-naphthoquinon-2-yl)pyrrole was thus obtained in a yield of 49% after chromatography on a column of silica.

Melting point: 75–76° C.

Example 10: Preparation of 1-Hexadecyl-2,5-bis(1,4-naphthoquinon-2-yl)pyrrole

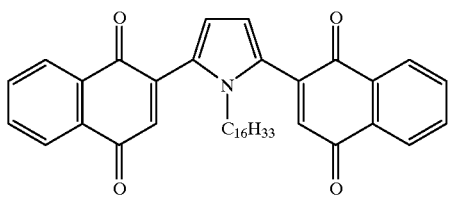

The same procedure as in Example 7 was followed by stirring 10 millimol of 1,4-naphthoquinone with 2.5 millimol of N-hexadecylpyrrole in 40 ml of acetic acid at 50° C. for 5 hours. The 1-hexadecyl-2,5-bis(1,4-naphthoquinon-2-yl)pyrrole was thus obtained in a yield of 38% after chromatography on a column of silica.

$^1$H NMR 200 MHz (CDCl$_3$, δ ppm): 0.8 to 1.5 (m, 31H), 4.00 (t, 2H), 6.63 (s, 2H), 7.05 (s, 2H), 7.74 to 7.85 (m, 4H), 8.06 to 8.23 (m, 4H). Melting point: 40–43° C.

Example 11: Preparation of 1-Benzyl-2,5-bis(1,4-naphthoquinon-2-yl)pyrrole

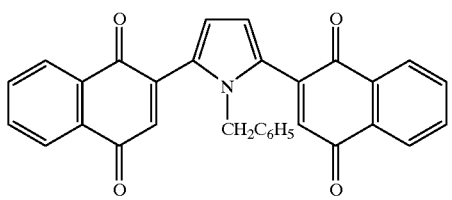

The same procedure as in Example 7 was followed by stirring 10 millimol of 1,4-naphthoquinone with 2.5 millimol of N-benzylpyrrole in 40 ml of acetic acid at 50° C. for 5 hours.

The 1-benzyl-2,5-bis(1,4-naphthoquinon-2-yl)pyrrole was thus obtained in a yield of 9% after chromatography on a column of silica.

Melting point: 149–150° C.

Example 12: Preparation of Methyl [5-(1,4-Dihydroxynaphthalen-2-yl)-1-methyl-1H-pyrrol-2-yl]acetate

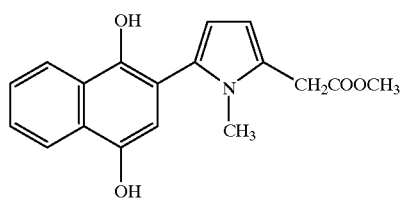

40 millimol of 1,4-naphthoquinone and 10 millimol of methyl 2-(N-methyl-1H-pyrrolyl)acetate were stirred in 50 ml of glacial acetic acid in a round-bottomed flask for 2 hours at room temperature. The reaction mixture was diluted with 300 ml of chloroform and the resulting mixture was then poured into a large volume of water (300 ml). The organic phase was then separated out and washed four times with 100 ml of water and finally with saturated aqueous NaCl solution. The resulting organic phase was dried over Na$_2$SO$_4$ and then concentrated under vacuum. The methyl [5-(1,4-dihydroxynaphthalen-2-yl)-1-methyl-1H-pyrrol-2-yl]acetate was thus isolated in a yield of 12% after purification by chromatography on a column of silica.

$^1$H NMR 200 MHz (DMSO-d$_6$, δ ppm): 3.35 (s, 3H), 3.66 (s, 3H), 3.86 (s, 2H), 5.97 (d, 1H), 6.02 (d, 1H), 6.64 (s, 1H), 7.41 to 7.52 (m, 2H), 8.05 to 8.17 (m, 2H), 8.45 (s, 1H), 9.56 (s, 1H). Melting point: 200–201° C.

Example 13: Preparation of Methyl [5-(1,4-Dioxo-1,4-dihydronaphthalen-2-yl)-1-methyl-1H-pyrrol-2-yl]acetate

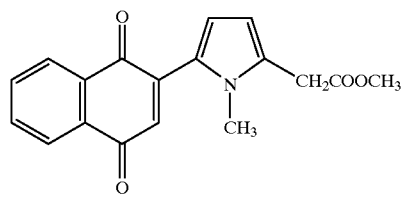

Working as in Example 12, methyl [5-(1,4-dioxo-1,4-dihydronaphthalen-2-yl)-1-methyl-1H-pyrrol-2-yl]acetate was also isolated by chromatography on a column of silica, in a yield of 56%.

$^1$H NMR 200 MHz (DMSO-d$_6$, δ ppm): 3.50 (s, 3H), 3.66 (s, 3H), 3.85 (s, 2H), 6.13 (d, 1H), 6.49 (d, 1H), 6.86 (s, 1H), 7.82 to 7.91 (m, 2H), 7.95 to 8.08 (m, 2H). Melting point: 89–90° C.

Example 14: Preparation of Methyl 4-(1,4-Dioxo-1,4-dihydronaphthalen-2-yl)-2,5-dimethyl-1H-pyrrole-3-carboxylate

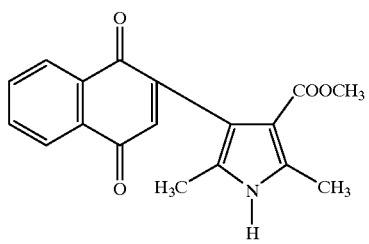

40 millimol of 1,4-naphthoquinone and 10 millimol of methyl 3-(2,5-dimethyl-1H-pyrrolyl)carboxylate were stirred in 50 ml of glacial acetic acid in a round-bottomed flask for 2 hours at room temperature. The reaction mixture was diluted with 300 ml of chloroform and the resulting mixture was then poured into a large volume of water (300 ml). The organic phase was then separated out and washed four times with 100 ml of water and finally with saturated aqueous NaCl solution. The resulting organic phase was dried over Na$_2$SO$_4$ and then concentrated under vacuum. The methyl 4-(1,4-dioxo-1,4-dihydronaphthalen-2-yl)-2,5-dimethyl-1H-pyrrole-3-carboxylate was thus isolated in a yield of a 39% after purification by chromatography on a column of silica.

$^1$H NMR 200 MHz (DMSO-d$_6$, δ ppm): 2.17 (s, 3H), 2.38 (s, 3H), 3.44 (s, 3H), 6.77 (s, 1H), 7.85 to 7.91 (m, 2H), 7.97 to 8.04 (m, 2H), 11.44 (broad s, 1H). Melting point: 209–210° C.

Example 15: Preparation of 2-(2,5-Dimethyl-1H-pyrrol-3-yl)-8-hydroxy-[1,4]-naphthoquinone

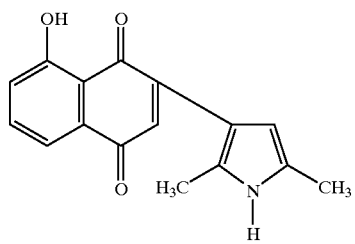

The same procedure as in Example 14 was followed, by stirring 40 millimol of 1,4-naphthoquinone and 10 millimol of 2,5-dimethyl-1H-pyrrole in 50 ml of glacial acetic acid in a round-bottomed flask for 2 hours at room temperature.

The product 2-(2,5-dimethyl-1H-pyrrol-3-yl)-8-hydroxy-[1,4]-naphthoquinone was thus isolated in a yield of 37% after purification by chromatography on a column of silica.

$^1$H NMR 200 MHz (DMSO-$d_6$, δ ppm): 2.15 (s, 3H), 2.30 (s, 3H), 6.14 (m, 1H), 6.68 (s, 1H), 7.30 (d.d, 1H), 7.48 (d.d, 1H), 7.73 (d.d, 1H), 11.0 (broad s, 1H), 12.11 (s, 1H). Melting point: 195–196° C.

Example 16: Preparation of Methyl 4-(8-Hydroxy-1,4-dioxo-1,4-dihydronaphthalen-2-yl)-1,2,5-trimethyl-1H-pyrrole-3-carboxylate

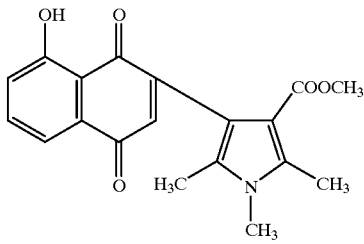

The same procedure as in Example 14 was followed, by stirring 40 millimol of 1,4-naphthoquinone and 10 millimol of methyl 3-(1,2,5-trimethyl-1H-pyrrolyl)carboxylate in 50 ml of glacial acetic acid in a round-bottomed flask for 2 hours at room temperature.

The product methyl 4-(8-hydroxy-1,4-dioxo-1,4-dihydronaphthalen-2-yl)-1,2,5-trimethyl-1H-pyrrole-3-carboxylate was thus isolated in a yield of 26% after purification by chromatography on a column of silica.

$^1$H NMR 200 MHz (DMSO-$d_6$, δ ppm): 2.19 (s, 3H), 2.47 (s, 3H), 3.46 (s, 3H), 3.48 (s, 3H), 6.74 (s, 1H), 7.36 (d.d, 1H), 7.55 (d.d, 1H), 7.78 (d.d, 1H), 11.9 (s, 1H). Melting point: 178–180° C. with decomposition.

Example 17: Preparation of Methyl 4-(8-Hydroxy-1,4-dioxo-1,4-dihydronaphthalen-2-yl)-2,5-dimethyl-1H-pyrrole-3-carboxylate

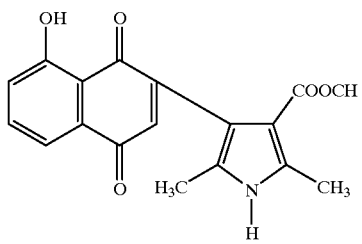

The same procedure as in Example 14 was followed, by stirring 40 millimol of 1,4-naphthoquinone and 10 millimol of methyl 3-(2,5-dimethyl-1H-pyrrolyl)carboxylate in 50 ml of glacial acetic acid in a round-bottomed flask for 2 hours at room temperature.

The product methyl 4-(8-hydroxy-1,4-dioxo-1,4-dihydronaphthalen-2-yl)-2,5-dimethyl-1H-pyrrole-3-carboxylate was thus isolated in a yield of 31% after purification by chromatography on a column of silica.

$^1$H NMR 200 MHz (DMSO-$d_6$, δ ppm): 2.17 (s, 3H), 2.39 (s, 3H), 3.48 (s, 3H), 6.77 (s, 1H), 7.36 (d.d, 1H), 7.55 (d.d, 1H), 7.78 (d.d, 1H), 11.47 (broad s, 1H), 11.91 (s, 1H). Melting point: 98–99° C. with decomposition.

Example 18: Preparation of 2-(1H-Pyrrol-2-yl)-[1,4]-naphthoquinone

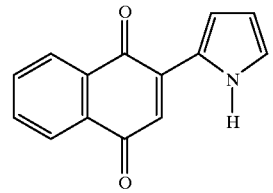

Using the procedure described in Example 1, starting with 3.16 millimol of 1,4-naphthoquinone, 25 millimol of pyrrole and 3.16 millimol of copper acetate in 50 ml of acetic acid, the product 2-(1H-pyrrol-2-yl)-[1,4]-naphthoquinone was isolated in a yield of 18% after purification by chromatography on a column of silica.

Melting point: 155–158° C.

Example 19: Preparation of 2-(4-Ethyl-3,5-dimethyl-1H-pyrrol-2-yl)-[1,4]-naphthoquinone

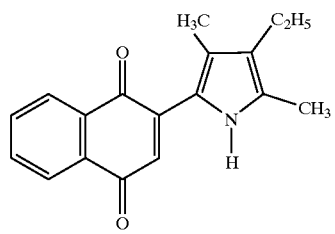

6.32 millimol of 1,4-naphthoquinone and 3.16 millimol of 2,4-dimethyl-3-ethylpyrrole were stirred in 20 ml of glacial acetic acid in a round-bottomed flask for 10 minutes at room temperature. The reaction mixture was diluted with 300 ml of dichloromethane and the resulting mixture was then poured into a large volume of water (300 ml). The organic phase was then separated out and washed four times with 100 ml of water and finally with saturated aqueous NaCl solution. The resulting organic phase was dried over $Na_2SO_4$ and then concentrated under vacuum. The product 2-(4-ethyl-3,5-dimethyl-1H-pyrrol-2-yl)-[1,4]-naphthoquinone was thus isolated in a yield of 80% after purification by chromatography on a column of silica.

$^1$H NMR 200 MHz ($CDCl_3$, δ ppm): 0.98 (t, 3H), 2.17 (s, 6H), 2.26 (q, 2H), 6.77 (s, 1H), 7.5 to 7.65 (m, 2H), 7.85 to 8.05 (m, 2H), 10.49 (broad s, 1H).

EXAMPLES OF DYE COMPOSITIONS

Example 20

The following dye composition was prepared:

| | |
|---|---|
| Dye prepared in Example 1 | 0.531 g |
| Benzyl alcohol | 10.0 g |
| Ethyl alcohol | 21.0 g |
| Glycerol | 5.0 g |
| Hydroxyethylcellulose sold under the name CELLOSIZE QP4400H by the company Union Carbide | 2.3 g |
| Citric acid | 1.4 g |
| Demineralized water qs | 100 g |

This dye composition was then applied to locks of permanent-waved grey hair containing 90% white hairs, at a rate of 3 grams per gram of hair. The composition was left to stand on the locks for 30 minutes at room temperature; the locks were then rinsed with running water and then dried.

The locks of hair were dyed a purple color.

Example 21

The following dye composition was prepared:

| | |
|---|---|
| Dye prepared in Example 5 | 0.702 g |
| Benzyl alcohol | 10.0 g |
| Ethyl alcohol | 21.0 g |
| Glycerol | 5.0 g |
| Hydroxyethylcellulose sold under the name CELLOSIZE QP4400H by the company Union Carbide | 2.3 g |
| Citric acid | 1.4 g |
| Demineralized water qs | 100 g |

This dye composition was then applied to locks of grey hair containing 90% white and bleached hairs, at a rate of 3 grams per gram of hair. The composition was left to stand on the locks for 30 minutes at room temperature; the locks were then rinsed with running water and then dried.

The locks of hair were dyed a beige-pink color.

Example 22

The following dye composition was prepared:

| | |
|---|---|
| Dye prepared in Example 7 | 0.881 g |
| Benzyl alcohol | 10.0 g |
| Ethyl alcohol | 21.0 g |
| Glycerol | 5.0 g |
| Hydroxyethylcellulose sold under the name CELLOSIZE QP4400H by the company Union Carbide | 2.3 g |
| Citric acid | 1.4 g |
| Demineralized water qs | 100 g |

This dye composition was then applied to locks of natural grey hair containing 90% white hairs, at a rate of 3 grams per gram of hair. The composition was left to stand on the locks for 30 minutes at room temperature; the locks were then rinsed with running water and then dried.

The locks of hair were dyed an intense coppery color.

Example 23

The following dye composition was prepared:

| | |
|---|---|
| Dye prepared in Example 1 | 0.500 g |
| Nonylphenol oxyethylenated with 9 mol of ethylene oxide | 8.0 g |
| Coconut acid diethanolamide | 2.0 g |
| Propylene glycol monomethyl ether | 10.0 g |
| 2-Amino-2-methyl-1-propanol qs | pH 9 |
| Demineralized water qs | 100 g |

This dye composition was then applied to locks of grey hair containing 90% white and bleached hairs, at a rate of 3 grams per gram of hair. The composition was left to stand on the locks for 30 minutes at room temperature; the locks were then rinsed with running water and then dried.

The locks of hair were dyed a pale salmon color.

Example 24

The following dye composition was prepared:

| | |
|---|---|
| Dye prepared in Example 7 | 0.881 g |
| Nonylphenol oxyethylenated with 9 mol of ethylene oxide | 8.0 g |
| Coconut acid diethanolamide | 2.0 g |
| Propylene glycol monomethyl ether | 10.0 g |
| 2-Amino-2-methyl-1-propanol qs | pH 9 |
| Demineralized water qs | 100 g |

This dye composition was then applied to locks of permanent-waved grey hair containing 90% white hairs, at a rate of 3 grams per gram of hair. The composition was left to stand on the locks for 30 minutes at room temperature; the locks were then rinsed with running water and then dried.

The locks of hair were dyed a very pale coppery color.

Example 25

The following dye composition was prepared:

| | |
|---|---|
| Dye prepared in Example 8 | 1.007 g |
| Nonylphenol oxyethylenated with 9 mol of ethylene oxide | 8.0 g |
| Coconut acid diethanolamide | 2.0 g |
| Propylene glycol monomethyl ether | 10.0 g |
| 2-Amino-2-methyl-1-propanol qs | pH 9 |
| Demineralized water qs | 100 g |

This dye composition was then applied to locks of grey hair containing 90% white and bleached hairs, at a rate of 3 grams per gram of hair. The composition was left to stand on the locks for 30 minutes at room temperature; the locks were then rinsed with running water and then dried.

The locks of hair were dyed a golden-blond color.

Example 26

The following dye composition was prepared:

| | |
|---|---|
| Dye prepared in Example 5 | 0.702 g |
| Nonylphenol oxyethylenated with 9 mol of ethylene oxide | 8.0 g |
| Coconut acid diethanolamide | 2.0 g |
| Propylene glycol monomethyl ether | 10.0 g |
| 2-Amino-2-methyl-1-propanol qs | pH 9 |
| Demineralized water qs | 100 g |

This dye composition was then applied to locks of grey hair containing 90% white and bleached hairs, at a rate of 3 grams per gram of hair. The composition was left to stand on the locks for 30 minutes at room temperature; the locks were then rinsed with running water and then dried.

The locks of hair were dyed a straw-yellow color.

Example 27

The following dye composition was prepared:

| | |
|---|---|
| Dye prepared in Example 11 | 1.052 g |
| Nonylphenol oxyethylenated with 9 mol of ethylene oxide | 8.0 g |
| Coconut acid diethanolamide | 2.0 g |
| Propylene glycol monomethyl ether | 10.0 g |
| 2-Amino-2-methyl-1-propanol qs | pH 9 |
| Demineralized water qs | 100 g |

This dye composition was then applied to locks of grey hair containing 90% white and bleached hairs, at a rate of 3 grams per gram of hair. The composition was left to stand on the locks for 30 minutes at room temperature; the locks were then rinsed with running water and then dried.

The locks of hair were dyed a golden-blond color.

Example 28

The following dye composition was prepared:

| | |
|---|---|
| Dye prepared in Example 12 | 0.934 g |
| Benzyl alcohol | 10.0 g |
| Ethyl alcohol | 21.0 g |
| Glycerol | 5.0 g |
| Hydroxyethylcellulose sold under the name CELLOSIZE QP4400H by the company Union Carbide | 2.3 g |
| Citric acid | 1.4 g |
| Demineralized water qs | 100 g |

This dye composition was then applied to locks of grey hair containing 90% white and bleached hairs, at a rate of 3 grams per gram of hair. The composition was left to stand on the locks for 30 minutes at room temperature; the locks were then rinsed with running water and then dried.

The locks of hair were dyed a pink color.

Example 29

The following dye composition was prepared:

| | |
|---|---|
| Dye prepared in Example 13 | 0.928 g |
| Benzyl alcohol | 10.0 g |
| Ethyl alcohol | 21.0 g |
| Glycerol | 5.0 g |
| Hydroxyethylcellulose sold under the name CELLOSIZE QP4400H by the company Union Carbide | 2.3 g |
| Citric acid | 1.4 g |
| Demineralized water qs | 100 g |

This dye composition was then applied to locks of grey hair containing 90% white and bleached hairs, at a rate of 3 grams per gram of hair. The composition was left to stand on the locks for 30 minutes at room temperature; the locks were then rinsed with running water and then dried.

The locks of hair were dyed a light-purple color.

Example 30

The following dye composition was prepared:

| | |
|---|---|
| Dye prepared in Example 14 | 0.928 g |
| Benzyl alcohol | 10.0 g |
| Ethyl alcohol | 21.0 g |
| Glycerol | 5.0 g |
| Hydroxyethylcellulose sold under the name CELLOSIZE QP4400H by the company Union Carbide | 2.3 g |
| Citric acid | 1.4 g |
| Demineralized water qs | 100 g |

This dye composition was then applied to locks of permanent-waved grey hair containing 90% white hairs, at a rate of 3 grams per gram of hair. The composition was left to stand on the locks for 30 minutes at room temperature; the locks were then rinsed with running water and then dried.

The locks of hair were dyed an intense beige-pink color.

Example 31

The following dye composition was prepared:

| | |
|---|---|
| Dye prepared in Example 15 | 0.827 g |
| Benzyl alcohol | 10.0 g |
| Ethyl alcohol | 21.0 g |
| Glycerol | 5.0 g |
| Hydroxyethylcellulose sold under the name CELLOSIZE QP4400H by the company Union Carbide | 2.3 g |
| Citric acid | 1.4 g |
| Demineralized water qs | 100 g |

This dye composition was then applied to locks of grey hair containing 90% white and bleached hairs, at a rate of 3 grams per gram of hair. The composition was left to stand on the locks for 30 minutes at room temperature; the locks were then rinsed with running water and then dried.

The locks of hair were dyed a pearlescent golden-grey color.

Example 32

The following dye composition was prepared:

| | |
|---|---|
| Dye prepared in Example 16 | 1.018 g |
| Benzyl alcohol | 10.0 g |
| Ethyl alcohol | 21.0 g |
| Glycerol | 5.0 g |
| Hydroxyethylcellulose sold under the name CELLOSIZE QP4400H by the company Union Carbide | 2.3 g |
| Citric acid | 1.4 g |
| Demineralized water qs | 100 g |

This dye composition was then applied to locks of permanent-waved grey hair containing 90% white hairs, at a rate of 3 grams per gram of hair. The composition was left to stand on the locks for 30 minutes at room temperature; the locks were then rinsed with running water and then dried.

The locks of hair were dyed a golden-blond color.

Example 33

The following dye composition was prepared:

| | |
|---|---|
| Dye prepared in Example 17 | 0.976 g |
| Benzyl alcohol | 10.0 g |
| Ethyl alcohol | 21.0 g |
| Glycerol | 5.0 g |
| Hydroxyethylcellulose sold under the name CELLOSIZE QP4400H by the company Union Carbide | 2.3 g |
| Citric acid | 1.4 g |
| Demineralized water qs | 100 g |

This dye composition was then applied to locks of grey hair containing 90% white and bleached hairs, at a rate of 3 grams per gram of hair. The composition was left to stand on the locks for 30 minutes at room temperature; the locks were then rinsed with running water and then dried.

The locks of hair were dyed a pale-coppery color.

Example 34

The following dye composition was prepared:

| | |
|---|---|
| Dye prepared in Example 18 | 0.5 g |
| Nonylphenol oxyethylenated with 9 mol of ethylene oxide | 8.0 g |
| Coconut acid diethanolamide | 2.0 g |
| Propylene glycol monomethyl ether | 10.0 g |
| 2-Amino-2-methyl-1-propanol qs | pH 9 |
| Demineralized water qs | 100 g |

This dye composition was then applied to locks of grey hair containing 90% white and bleached hairs, at a rate of 3 grams per gram of hair. The composition was left to stand on the locks for 30 minutes at room temperature; the locks were then rinsed with running water and then dried.

The locks of hair were dyed a beige-pink color.

Example 35

The following dye composition was prepared:

| | |
|---|---|
| Dye prepared in Example 19 | 0.838 g |
| Benzyl alcohol | 10.0 g |
| Ethyl alcohol | 21.0 g |
| Glycerol | 5.0 g |
| Hydroxyethylcellulose sold under the name CELLOSIZE QP4400H by the company Union Carbide | 2.3 g |
| Citric acid | 1.4 g |
| Demineralized water qs | 100 g |

This dye composition was then applied to locks of grey hair containing 90% white and bleached hairs, at a rate of 3 grams per gram of hair. The composition was left to stand on the locks for 30 minutes at room temperature; the locks were then rinsed with running water and then dried.

The locks of hair were dyed a silvery lavender-blue color.

We claim:

1. A compound of formula (I) or (II):

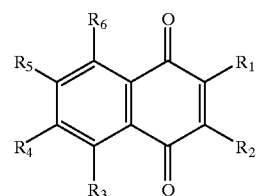

(I)

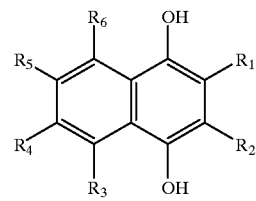

(II)

wherein, in said formulae (I) or (II):

$R_1$ and $R_2$ are independently selected from a hydrogen atom, an OH radical, $C_1$–$C_4$ alkyl radicals, $C_1$–$C_4$ alkoxy radicals and a radical Z of formula (III):

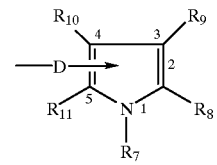

(III)

$R_3$ to $R_6$ independently are selected from a hydrogen atom, halogen atoms, an OH radical, $C_1$–$C_4$ alkyl radicals and $C_1$–$C_4$ alkoxy radicals, D is a covalent bond between the pyrrole ring (III) and the ring of structure (I) or (II), $R_7$ to $R_{11}$ independently are chosen from a hydrogen, optionally substituted $C_1$–$C_{18}$ alkyl radicals, $SO_2$—$C_6H_5$, $CO(C_1$–$C_4)$alkyl radicals, a $CH_2C_6H_5$ radical, COOH and salts thereof, $COO(C_1$–$C_4)$alkyl radicals, CONR'R" wherein R' and R" independently are chosen from H, and $C_1$–$C_4$ alkyl radicals, and $C_6H_5$ radicals which may be substituted with one or more halogen atoms or one or more hydroxyl groups, $C_1$–$C_4$ alkyl radicals, or C$_1$–C$_4$ alkoxy radicals, and R$_8$ to R$_{11}$ may also denote at least one bond D, wherein
(i) at least one of the radicals R$_1$ and R$_2$ denotes a radical Z, and
(ii) the attachment of Z to the rings of formulae (I) or (II) is carried out on any of the positions 2 to 5 of the pyrrole ring of formula (III), and wherein the following compounds are excluded:
2-(1-benzenesulphonyl-1H-pyrrol-2-yl)-[1,4]-naphthoquinone,
2-(1-benzyl-1H-pyrrol-2-yl)-3-methoxy-[1,4]-naphthoquinone,
2-(1-ethyl-1H-pyrrol-2-yl)-3-methoxy-[1,4]-naphthoquinone,
2-(1H-pyrrol-2-yl)-3-methoxy-[1,4]-naphthoquinone,
2-(1-methyl-1H-pyrrol-2-yl)-3-methyl-[1,4]-naphthoquinone,
2-(1-methyl-1H-pyrrol-2-yl)-3-methoxy-[1,4]-naphthoquinone,
1-methyl-2,5-bis-([1,4]-dihydroxynaphthalene)-pyrrole,
2-(2,5-diethyl-1-methyl-pyrrol-3-yl)-[1,4]-naphthoquinone,
2-(1-methyl-1H-pyrrol-2-yl)-[1,4]-dihydroxynaphthalene, and
compounds of formula (IV):

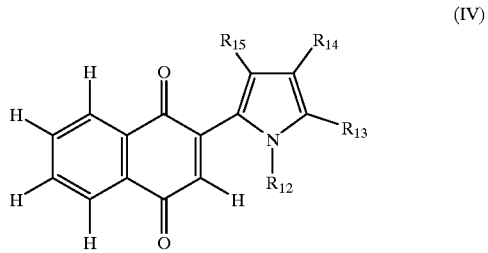

in which:
R$_{12}$ is chosen from H, alkyl, aryl and aralkyl groups and
R$_{13}$, R$_{14}$ and R$_{15}$ independently are chosen from H, alkyl, aryl, and SO$_2$—C$_6$H$_5$.

2. A compound according to claim 1, wherein said compound is selected from:
2-(1,2,5-trimethyl-1H-pyrrol-4-yl)-[1,4]-naphthoquinone,
3-[2-(1,4-dioxo-1,4-dihydronaphthalen-2-yl)pyrrol-1-yl]propionitrile,
methyl [5-(1,4-dioxo-1,4-dihydronaphthalen-2-yl)-1-methyl-1H-pyrrol-2-yl]acetate,
methyl 4-(1,4-dioxo-1,4-dihydronaphthalen-2-yl)-2,5-dimethyl-1H-pyrrole-3-carboxylate,
methyl 4-(1,4-dioxo-1,4-dihydronaphthalen-2-yl)-1,2,5-trimethyl-1H-pyrrole-3-carboxylate,
2-(2,5-dimethyl-1H-pyrrol-3-yl)-8-hydroxy-[1,4]-naphthoquinone,
methyl 4-(8-hydroxy-1,4-dioxo-1,4-dihydronaphthalen-2-yl)-1,2,5-trimethyl-1H-pyrrole-3-carboxylate,
methyl 4-(8-hydroxy-1,4-dioxo-1,4-dihydronaphthalen-2-yl)-2,5-dimethyl-1H-pyrrole-3-carboxylate,
2-(2,5-dimethyl-1H-pyrrol-3-yl)-[1,4]-naphthoquinone,
2-[1-(β-hydroxyethyl)-1H-pyrrol-2-yl]-[1,4]-naphthoquinone,
N-{2-[2-(1,4-dioxo-1,4-dihydronaphthalen-2-yl)pyrrol-1-yl]ethyl}acetamide,
2-{N-[(2-hydroxy-1-hydroxymethyl-1-methyl)ethyl]-1H-pyrrol-2-yl}-[1,4]-naphthoquinone,
2-carboxymethyl-5-(1,4-dioxo-1,4-dihydronaphthalen-2-yl)-1,4-dimethyl-1H-pyrrole-3-carboxylic acid,
4-(1,4-dioxo-1,4-dihydronaphthalen-2-yl)-2,5-dimethyl-1H-pyrrole-3-carboxylic acid,
ethyl 4-(1,4-dioxo-1,4-dihydronaphthalen-2-yl)-3,5-dimethyl-1H-pyrrole-2-carboxylate, and
2-(4-acetyl-3,5-dimethyl-1H-pyrrol-2-yl)-[1,4]-naphthoquinone.

3. A dye composition for a keratin substance comprising, in a medium suitable for dyeing, an effective amount of at least one compound of formula (I) or formula (II) as defined in claim 1.

4. A dye composition according to claim 3, wherein said keratin substance is a human keratin substance.

5. A dye composition according to claim 4, wherein said human keratin substance is human hair.

6. A dye composition according to claim 3, wherein said dye composition has a pH ranging from 2 to 11.

7. A dye composition according to claim 6, wherein said dye composition has a pH ranging from 2.5 to 10.

8. A dye composition according to claim 3, wherein said at least one compound is present in an amount ranging from 0.01 to 10% by weight relative to the total weight of said dye composition.

9. A dye composition according to claim 8, wherein said at least one compound is present in an amount ranging from 0.05 to 5% by weight relative to the total weight of said dye composition.

10. A dye composition according to claim 3, wherein said medium suitable for dyeing comprises water or water and at least one organic solvent.

11. A dye composition according to claim 10, wherein said at least one organic solvent is selected from alcohols, glycols and glycol ethers.

12. A dye composition according to claim 10, wherein said at least one organic solvent is present in a concentration ranging from 0.5 to 25% by weight relative to the total weight of said dye composition.

13. A dye composition according to claim 3, wherein said dye composition further comprises at least one additional direct dye.

14. A dye composition according to claim 13, wherein said at least one additional direct dye is present in a concentration ranging from 0.05 to 10% by weight, relative to the total weight of said dye composition.

15. A dye composition according to claim 3, wherein said composition is in the form of a liquid, cream, gel, or any form suitable for dyeing keratin substances.

16. A process for directly dyeing human keratin fibers comprising
applying an effective amount of at least one dye composition according to claim 3 to wet or dry keratin fibers,
leaving said composition on said fibers for an exposure time ranging from 3 to 60 minutes,
rinsing said fibers,
optionally washing and rinsing said fibers again, and
drying said fibers.

17. A process according to claim 16, wherein said dye composition contains methyl [5-(1,4-dihydroxynaphthalen-2-yl)-1-methyl-1H-pyrrol-2-yl]acetate.

18. A process according to claim 16, wherein said human keratin fibers are human hair.

19. A process according to claim 16, wherein said exposure time ranges from 5 to 45 minutes.

20. A process for directly dyeing human keratin fibers comprising
applying at least one composition according to claim 3 to wet or dry keratin fibers, and
if said keratin fibers are wet, drying said keratin fibers.

21. A process according to claim 20, wherein said human keratin fibers are human hair.

22. A process for dyeing human keratin fibers comprising applying an effective amount of a composition according to claim 3 to said fibers.

23. A process according to claim 22, wherein said human keratin fibers are human hair.

24. A process for directly dyeing human keratin fibers comprising applying to wet or dry keratin fibers an effective amount of at least one dye composition containing a compound of formula (I) or (II):

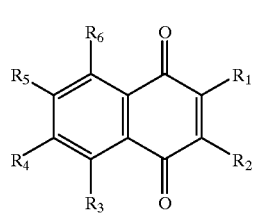

(I)

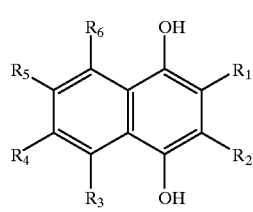

(II)

wherein, in said formulae (I) or (II):

$R_1$ and $R_2$ are independently selected from a hydrogen atom, halogen atoms, an OH radical, $C_1$–$C_4$ alkyl radicals, $C_1$–$C_4$ alkoxy radicals and a radical Z of formula (III):

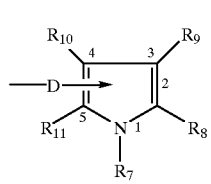

(III)

$R_3$ to $R_6$ independently are selected from a hydrogen atom, halogen atoms, an OH radical, $C_1$–$C_4$ alkyl radicals and $C_1$–$C_4$ alkoxy radicals, D is a covalent bond between the pyrrole ring (III) and the ring of structure (I) or (II), $R_7$ to $R_{11}$ independently are selected from hydrogen, optionally substituted $C_1$–$C_{18}$ alkyl radicals, $SO_2$—$C_6H_5$, $CO(C_1$–$C_4)$alkyl radicals, a $CH_2C_6H_5$ radical, COOH and salts thereof, $COO(C_1$–$C_4)$alkyl radicals, CONR'R" wherein R' and R" independently denote H or $C_1$–$C_4$ alkyl radicals, and a $C_6H_5$ radical which may be substituted with one or more halogen atoms or one or more hydroxyl, $C_1$–$C_4$ alkyl or $C_1$–$C_4$ alkoxy radicals, and $R_8$ to $R_{11}$ may also denote at least one bond D, wherein (i) at least one of the radicals $R_1$ and $R_2$ denotes a radical Z, and (ii) the attachment of Z to the rings of formulae (I) or (II) is carried out on any of the positions 2 to 5 of the pyrrole ring of formula (III), leaving said composition on said fibers for an exposure time ranging from 3 to 60 minutes, rinsing said fibers, optionally washing and rinsing said fibers again, and drying said fibers.

25. A compound selected from:

1-pentyl-2,5-bis(1,4-naphthoquinon-2-yl)pyrrole, 1-octyl-2,5-bis(1,4-naphthoquinon-2-yl)pyrrole, 1-hexadecyl-2,5-bis(1,4-naphthoquinon-2-yl)pyrrole, and 1-benzyl-2,5-bis(1,4-naphthoquinon-2-yl)pyrrole.

26. A method for directly dyeing human keratin fibers, comprising: applying an effective amount of at least one dye composition comprising, in a medium suitable for dyeing, an effective amount of 2-(1-methyl-1H-pyrrol-2-yl)-[1,4]-dihydroxynaphthalene to wet or dry keratin fibers, leaving said composition on said fibers for an exposure time ranging from 3 to 60 minutes, rinsing said fibers, optionally washing and rinsing said fibers again, and drying said fibers.

* * * * *